United States Patent
Shen (10) Patent No.: US 9,258,300 B2
(45) Date of Patent: Feb. 9, 2016

(54) ECG MEASURING DEVICE AND METHOD THEREOF

(71) Applicant: Tzu Chi University, Hualien County (TW)

(72) Inventor: Tsu-Wang Shen, Hualien County (TW)

(73) Assignee: TZU CHI UNIVERSITY, Hualien, Hualien County (TW)

( * ) Notice: Subject to any disclaimer, the term of this patent is extended or adjusted under 35 U.S.C. 154(b) by 98 days.

(21) Appl. No.: 14/066,029

(22) Filed: Oct. 29, 2013

(65) Prior Publication Data

US 2014/0120876 A1 May 1, 2014

Related U.S. Application Data

(60) Provisional application No. 61/719,889, filed on Oct. 29, 2012.

(51) Int. Cl.

| | |
|---|---|
| G06F 21/00 | (2013.01) |
| H04L 29/06 | (2006.01) |
| H04W 12/06 | (2009.01) |
| A61B 5/0452 | (2006.01) |
| A61B 5/00 | (2006.01) |
| A61B 5/117 | (2006.01) |
| G06K 9/00 | (2006.01) |

(52) U.S. Cl.
CPC ........ *H04L 63/0861* (2013.01); *A61B 5/04525* (2013.01); *A61B 5/117* (2013.01); *A61B 5/6898* (2013.01); *G06K 9/00536* (2013.01); *G06K 9/00885* (2013.01); *H04W 12/06* (2013.01); *G06K 2009/00939* (2013.01)

(58) Field of Classification Search
CPC ...................... A61B 2560/0468; A61B 5/0404; A61B 5/04525; A61B 5/6898; A61B 5/117; A61B 5/0408; A61B 5/04082; A61B 5/04087; A61B 5/0402; H04W 12/06; G06K 9/00536; G06K 2009/00939; G06K 9/00885; H04L 63/0861

See application file for complete search history.

(56) References Cited

U.S. PATENT DOCUMENTS

| | | | | |
|---|---|---|---|---|
| 6,549,756 | B1 * | 4/2003 | Engstrom | 455/66.1 |
| 7,801,594 | B1 * | 9/2010 | Higham | 600/515 |
| 2005/0239493 | A1 * | 10/2005 | Batkin et al. | 455/550.1 |
| 2006/0217623 | A1 * | 9/2006 | Morganroth | 600/509 |
| 2007/0021677 | A1 * | 1/2007 | Markel | 600/509 |
| 2010/0076331 | A1 * | 3/2010 | Chan et al. | 600/522 |
| 2010/0090798 | A1 * | 4/2010 | Garcia Molina | G06K 9/0055 340/5.53 |
| 2012/0206485 | A1 * | 8/2012 | Osterhout et al. | 345/633 |
| 2013/0109946 | A1 * | 5/2013 | Shim et al. | 600/386 |

* cited by examiner

*Primary Examiner* — Shewaye Gelagay
*Assistant Examiner* — Amie C Lin
(74) *Attorney, Agent, or Firm* — Muncy, Geissler, Olds & Lowe, P.C.

(57) ABSTRACT

The present invention discloses at least two electrodes disposed at the body of the ECG measuring device of the present invention. When a user normally uses the ECG measuring device, the two electrodes are just adhered to the hands and the face of the user. The ECG measuring method of the present invention is to measure a first ECG signal from the left hand to the left side of face of the user and a second ECG signal from the right hand to the right side of face of the user. Then a plurality of ECG features are obtained from the first ECG signal, the second ECG signal and the result, as related coefficients, of the interactive computing, as a method of plus and subtract, of the first ECG signal and the second ECG signal. Hence, a biometric authorization process is engaged according to the plurality of ECG features.

12 Claims, 10 Drawing Sheets

ECG MEASURING DEVICE AND METHOD THEREOF

BACKGROUND OF THE INVENTION

1. Field of the Invention

The present invention generally relates to a measuring device and a method thereof, more particularly to a measuring device and a method thereof that are for measuring an electrocardiogram (ECG).

2. Description of the Related Art

In recent years, people are gradually increasing the requirements for security verification. For instance, personal password, ID number, access control card, or biometric identification is broadly extended to our normal life.

According to statistics, people spend at least fourteen minutes per day to use portable phones. Because of the increasing trend for people having portable phones, the persons skilled in the art have proposed variety methods, in order to combine users' verification or identification information on portable phones for various security reasons. For example, the verification or identification process can be engaged through portable phones so as to facilitate payment of small amount money for general daily consumptions.

However, for the current verification or identification system on a portable phone, the user still needs additional steps to operate, such as inputting password, address, ID number, etc., or an extra device, such as ID or sensing card. Moreover, even if the biometric verification or identification system is built in a portable phone, the user may still need extra time to look at the lens of a camera for capturing iris information, or press the specific portions of the portable phone for capturing a fingerprint or measuring an ECG signal. Hence it is very inconvenient and non-passive.

As aforesaid biometric verification or identification, the user utilizes the portable phone to obtain biometric characteristics, so additional time and redundant acts have to be preformed. It is not convenient for general users. In addition, recent verification and identification methods could not effectively use the calling time to measure, determine and verify identity and emotion. This invention passively measures the biometric characteristics when the user is normally using a portable phone, such as speaking during a phone call.

Accuracy of the biometric identification is a critical problem. The present technology is able to use an ECG for human identification. However, the prior Lead-I ECG based identification methods have fewer characteristics on signals. Hence, accuracy is hardly improved because it is lack of distinguishable biometric features. The above reasons make current ECG biometrics hardly applied in the field of high security applications.

SUMMARY OF THE INVENTION

The main objective of the present invention is to provide an electrocardiogram (ECG) measuring device and a method thereof, that is, a Lead-I ECG is divided into a plurality of parts corresponding to the natural physiological structure of a body. The accuracy of ECG identification is improved based on this measurement method. Because the physiological phenomenon is different from person to person, it cannot be directly observable through human eyes or skin touch. That makes biometrics hard to be duplicated.

The second objective of the present invention is to provide the passive ECG measuring device and the method thereof, that is, when a user is normally using a device such as a cellular phone, a passive ECG measurement simultaneously applied at the same time through a plurality of electrodes at the device body.

To approach above objectives, at least two electrodes are disposed at the body of the ECG measuring device of the present invention. When the user normally uses the ECG measuring device, the two electrodes are just adhered to one hand and the face of the user. The proposed ECG measuring method is to measure a first ECG signal from the left hand to the left side of face of the user and a second ECG signal from the right hand to the right side of face of the user. Then a plurality of ECG features are obtained from the first ECG signal, the second ECG signal and the combinations of the first and second signals, which includes such as correlation coefficients, and any linear combinations of two signals. ECG biometric process can engage with the plurality of ECG features.

The effects that can be achieved according to the present invention are described as below. The present invention uses a portable device, such as a smart phone, to be a measurement device, and portions of the casing body of the measuring device can place electrodes, such as a front surface, a back surface, a plurality of lateral surfaces, and a display screen. Therefore, when the user normally uses the portable device to receive a phone call, the ECG is simultaneously, passively measured without extra time needed.

Further, the present invention divides the regular Lead-I ECG from the left hand to the right hand into two subset signals based on the characteristics of a human body. One subset signal is from the left hand to the left side of face of the user and the other subset signal is from the right hand to the right side of face of the user. In brief, one is so-call "the first ECG signal" and the other is so-call "the second ECG signal". By engaging the interactive computing of the two subset ECG signals can obtain more information than regular Lead-I ECG. As a result, the amount of the identify verification features can be more than double by comparison with regular Lead-I ECG, and the accuracy of verification and identification will be increased at the same time in proportional.

BRIEF DESCRIPTION OF THE DRAWINGS

The objects, spirits, and advantages of the preferred embodiments of the present invention will be readily understood by the accompanying drawings and detailed descriptions, wherein.

DETAILED DESCRIPTION OF THE INVENTION

Following preferred embodiments and figures will be described in detail so as to achieve aforesaid objects.

Please refer to FIG. 1, FIG. 2, FIG. 3, and FIG. 4, which illustrates schematic front and back views of an embodiment of the ECG measuring device of the present invention, a schematic measuring view of an embodiment of the ECG measuring device of the present invention. For the embodiment, the measuring device 1 can be a portable device, such as a smart phone, but not limited thereto.

Figure 1:
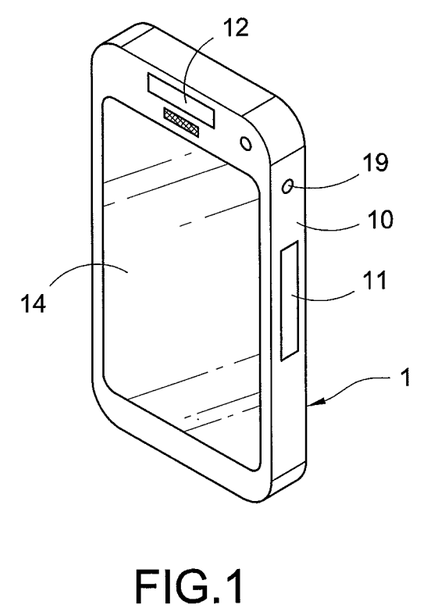
FIG. 1 illustrates a schematic front view of an embodiment of the ECG measuring device of the present invention.
Figure 2:
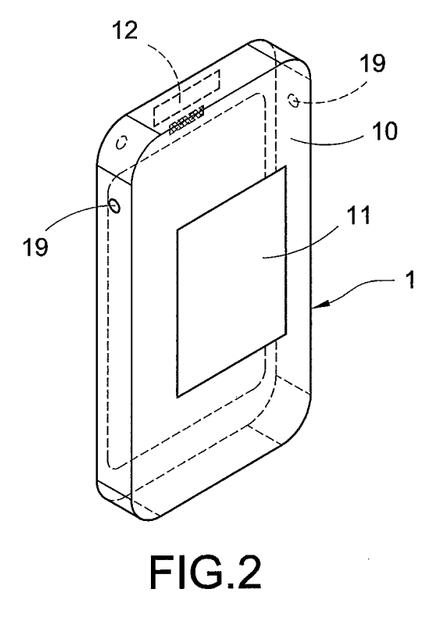
FIG. 2 illustrates a schematic back view of an embodiment of the ECG measuring device of the present invention.

A plurality of electrodes are disposed on the body of the measuring device 1. For example, a first electrode 11 is disposed at the lateral surface or the back surface of the casing 10 of the measuring device 1, and a second electrode 12 is disposed at the front surface of the casing 10 of the measuring device 1. Moreover, the electrodes 11 and 12 can be directly disposed on a display screen 14 of the measuring device 1 if the electrodes 11 and 12 are made of graphene, which is almost transparent. Hence, without effecting the normal operations of the display screen 14, the electrodes 11 and 12 can be disposed on the display screen 14. The electrodes 11 and 12 disposed on the casing 10 is an example and described as following, but not limited thereto.

The present invention uses the two electrodes 11 and 12 to touch the hands 21 and the face 22 of a user 2 under the user 2 normally using the measuring device 1, for example, making/receiving a telephone call. Through the present invention, the user 2 may not need an additional measuring action other than making general phone calls, and the measuring device 1 is able to measure during calling time.

The measuring device 1 uses the first electrode 11 to touch the hands of the user 2 and the second electrode 12 to touch the face of the user 2 when the user 2 is making/receiving a telephone call. The only requirement is to effectively touch the user 2, the positions of the electrodes 11 and 12 are adjustable and are not limited thereto by the figures.

As shown in FIG. 1, the first electrode 11 is disposed at the lateral surface of the casing 10 in order to let the first electrode 11 touch the finger(s) of the user 2. As shown in FIG. 2, the first electrode 11 is disposed at the back surface of the casing 10 in order to let the first electrode 11 touch the palm of the user 2. Moreover, the second electrode 12 is preferably disposed at the top of the front surface of the casing 10 in order to let the second electrode 12 touch the ear/face of the user 2, but not limited thereto. As aforesaid, the two electrodes 11 and 12 are made of graphene and are directly disposed on the display screen 14. The electrodes 11 and 12 directly touch the user 2, so the electrodes 11 and 12 are exposed to the casing 10 or the display screen 14. Or, the partial areas of the casing 10 or the display screen 14 are made of conductive material, and therefore the electrodes 11 and 12 can be disposed in the casing 10 or the display screen 14 and touch the user 2 via the partial areas.

The Lead-I ECG is to measure a circuit vector from the left hand to the right hand of a user. The technical explanation of the present invention is to divide the vector into two parts, including a vector from left hand to the center line of a body and the other vector from the center line of a body to right hand. The physiological descriptions include the measurement from the left hand to the left side of face and the measurement from the right hand to the right side of face. It has to be noted that the present invention divides the Lead-I ECG into two parts based on the natural body anatomy of a human being, which causes amount of identifying features increased. Therefore the accuracy rate of identification is also increased significantly. The two circuit vectors are various from person to person, and those variances cannot be seen by eyes. Hence, the security is further improved.

The present invention divides the traditional Lead-I ECG into two parts in order to have a right hand to face ECG and a left hand to face ECG for obtaining more physical information. Such ECG signals can extract respiratory signals and measure specific diseases which are related with the right of a heart.

In addition, depending on the anatomy characteristics of a human body, the traditional Lead-I ECG measuring from the left hand to the right hand is divided into two subsets, which are an ECG A signal measuring from the left hand to the left side of face and an ECG B signal measuring from the right hand to the right side of face. However, because of body nature characteristics, adding the ECG A and B signals together is not equal to a traditional Lead-I ECG from the left hand to the right hand. The relationship is listed as a formula below:

Lead-*I* ECG(traditional Lead-*I*)=Lead-*I* ECG(right; ECG *B*)+Lead-*I* ECG(left;ECG *A*)+Remaining components.

According to above formula, the traditional Lead-I ECG is separated three components. Hence, through the measurement method, the remaining component as a third ECG signal produces by the traditional Lead-I ECG and two subset ECGs. It can be a higher level security key because it cannot be known only if the system knows all traditional Lead-I ECG and two subset components. In fact, the amount of identified features and the accuracy rate can significantly increase to solve the problem that the Lead-I ECG lacks identity features in high security applications.

Figure 3:
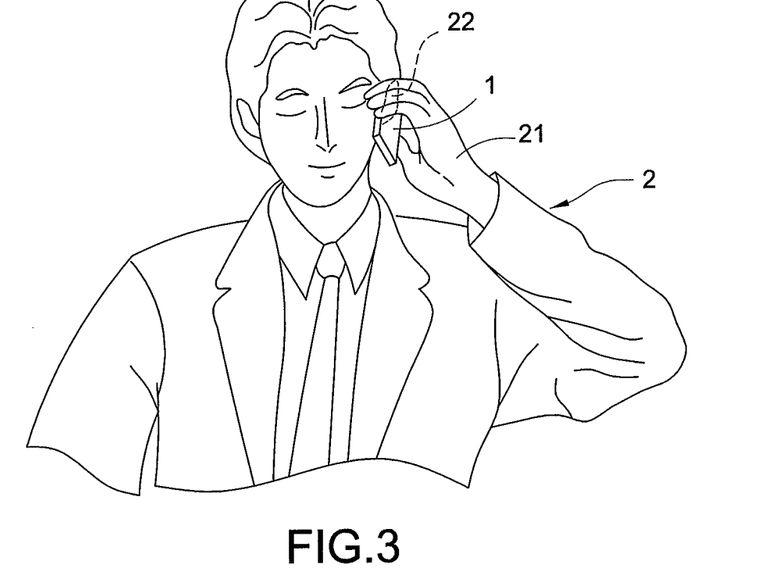
FIG. 3 illustrates a schematic measuring view of a first ECG signal of an embodiment of the ECG measuring device of the present invention.
Figure 4:
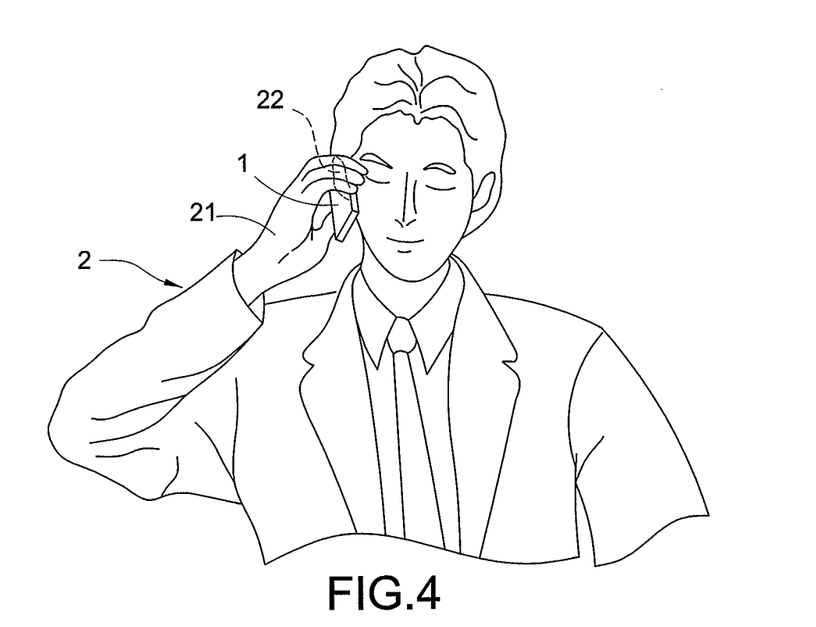
FIG. 4 illustrates a schematic measuring view of a second ECG signal of an embodiment of the electrocardiogram (ECG) measuring device of the present invention.

As shown in FIG. 3 and FIG. 4, the two electrodes 11 and 12 are attached to the left hand and the left side of face of the user 2. In order to apply left hand to the left side of face to measure the first ECG signal-31 shown in FIG. 7B, the left ear is a preferable place to touch. Similarly, the two electrodes 11 and 12 are attached to the right hand and the right side of face of the user 2. In order to apply the right hand to the right side of face to measure the second ECG signal 32 shown in FIG. 7C, the right ear is a preferable location to touch.

The major effect by dividing the traditional Lead-I ECG into two parts is to obtain at least the double amount of the ECG features from extraction of the two ECG signals 31 and 32. If the traditional Lead-I ECG has n features by any feature extraction method, then this invention provides at least 2n available ECG features.

Figure 5:
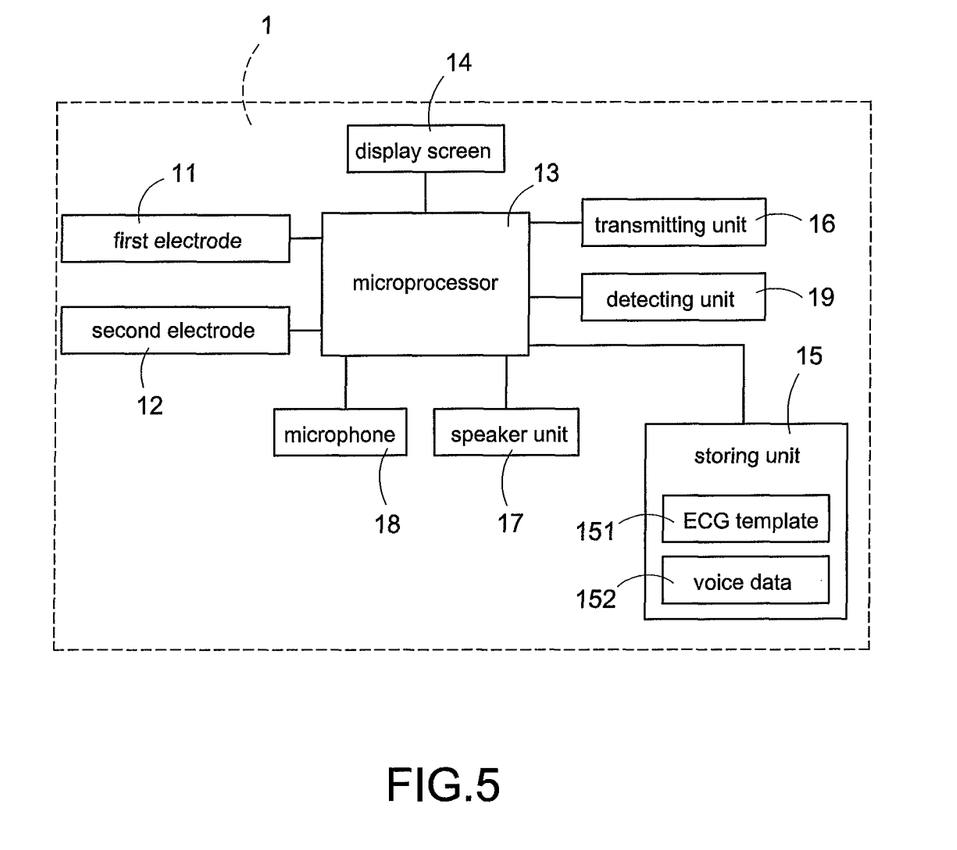
FIG. 5 illustrates a schematic block diagram of an embodiment of the ECG measuring device of the present invention.

Please refer to FIG. 5, which illustrates a schematic block diagram of an embodiment of the ECG measuring device of the present invention. The ECG measuring device 1 includes the first electrode 11, the second electrode 12, a microprocessor 13, and the display screen 14. The microprocessor 13 is electrically connected with the first electrode 11, the second electrode 12 and the display screen 14. The first electrode 11, the second electrode 12 and the display screen 14 are exposed to the casing 10, and the microprocessor 13 is placed in the casing 10. The two electrodes 11 and 12 can be directly disposed on the display screen 14, but not limited thereto.

The microprocessor 13 mainly senses and samples the two electrodes 11 and 12 when the two electrodes 11 and 12 touch the left hand and the left side of face of the user 2. Then the microprocessor 13 captures the first ECG signal 31. Similarly, the two electrodes 11 and 12 touch the right hand and the right side of face of the user 2 to capture the second ECG signal 32. In the meantime, the first ECG signal 31 and the second ECG signal 32 are engaged in signal processes by the microprocessor 13, for example, signal amplifying, analog/digital conversion, and filtering etc. Aforesaid processes are very common in the field and may not be described any further.

When measuring the first ECG signal 31 and the second ECG signal 32 is done, via aforesaid feature extraction method, ECG features with a preset amount are extracted from the first ECG signal 31, and ECG features with a preset amount are extracted from the second ECG signal 32. The measuring device 1 is able to engage in the biometric authorization process for the user 2 through these ECG features. The measuring device 1 uses the display screen 14 to present the two ECG signals 31 and 32, the ECG features, the biometric authorization results, etc., so that the user 2 is noted.

For the embodiment, the measuring device 1 comprises at least one detecting unit 19 that is electrically connected with the microprocessor 13. As shown in FIG. 1 and FIG. 2, the amount of the detecting unit 19 is preferably two, and the two detecting units 19 are disposed at two sides of the casing 10 and are exposed to the outside of the casing 10. For the embodiment, the detecting unit 19 is preferably a light sensor. Hence, when the user 2 uses the left hand to hold the measuring device 1, the light emitted from the detecting unit 19 at the left side of the casing 10 is blocked by the thumb of the left hand, so the measuring device 1 determines that the present measurement is for the first ECG signal 31 of the left hand to the left side of face; on the contrary, when the user 2 uses the right hand to hold the measuring device 1, the light emitted from the detecting unit 19 at the right side of the casing 10 is blocked by the thumb of the right hand, so the measuring device 1 determines that the present measurement is for the second ECG signal 32 of the right hand to the right side of face. For another embodiment, the detecting unit 19 is preferably fingerprint sensors. Hence, the detecting unit 19 detects user's 2 fingerprints on both hands separately, so the measuring device 1 can determine that the present measurement is for the first ECG signal 31 of the left hand to the left side of face, or for the second ECG signal 32 of the right hand to the right side of face.

The measuring device 1 further comprises a storing unit 15. The storing unit 15 is disposed in the casing 10 and is electrically connected with the microprocessor 13. The storing unit 15 stores at least one ECG template 151. In practice, for the enrollment process, the user 2 may register the first ECG signal 31 and the second ECG signal 32 to store those signals or features in the storing unit 15 in advance as the ECG templates 151. When the biometric authorization process is being engaged, the microprocessor 13 mainly processes the two input ECG signals 31 and 32. After the ECG features are extracted, the microprocessor 13 compares the ECG features or waveforms with the existed ECG templates 151 so as to determine whether the user 2 passes the biometric authorization process. For example, a related program can be embedded into the microprocessor 13, and the microprocessor 13 applied methods such as the time domain analysis, the spectral analysis, feature vector analysis and the entropy analysis for matching ECG templates of the user 2, but not limited thereto.

In general, the microprocessor 13 extracts the ECG features from the two ECG signals 31 and 32, and thus extracts the corresponding ECG features from the ECG template 151. The template 151 has the same amount of features to match the amount of the ECG features from the two ECG signals 31 and 32. The microprocessor matches those features in order to determine whether the user 2 passes the biometric authorization process. It is to be noted that the ECG template 151 is measured, enrolled, and stored by the measuring device 1; on the contrary, some other devices are also able to measure the user 2 and then transmits the result to the measuring device 1 to store, but not limited thereto.

Figure 8:
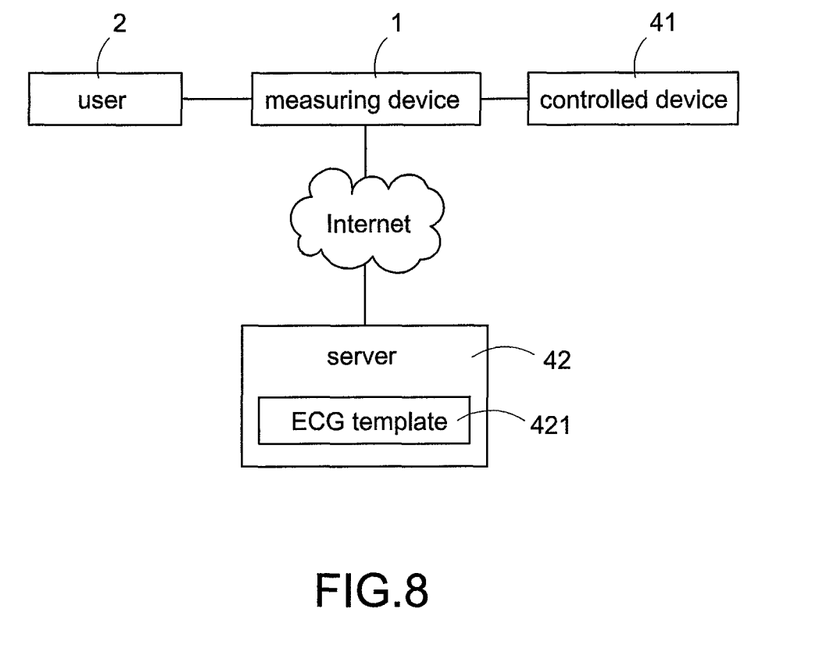
FIG. 8 illustrates a schematic view of identification processes of an embodiment of the ECG measuring device and the method thereof of the present invention.

The measuring device 1 further has a transmitting unit 16. The transmitting unit 16 is implemented in the casing 10 and is electrically connected with the microprocessor 13. As aforesaid, the measuring device 1 extracts the ECG features via the microprocessor 13, and the ECG features are matched with the ECG template 151. For another embodiment, the measuring device 1 only uses the two electrodes 11 and 12 to measure ECG signals, and next the microprocessor 13 amplifies ECG signals, converts from analog to digital, etc. Then such processed data are transmitted to an external server 42, as shown in FIG. 8, via the transmitting unit 16. The server 42 stores the ECG template 421 measured by the user in advance. Hence, the server 42 is able to engage in the biometric authorization process for the user 2.

However, the measuring device 1 or the server 42 engaging in the biometric authorization process shall depend on practical conditions, but not limited thereto. If the measuring device 1 is to execute the biometric authorization process, the microprocessor 13 may have the function to extract ECG features from the two ECG signals 31 and 32, and the user 2 may measure the ECG template 151 and store the ECG template 151 in the measuring device 1 in advance. On the other hand, if the server 42 is to execute the biometric authorization process, the server 42 may be able to receive the two ECG signals 31 and 32, and extract the ECG features from the two ECG signals 31 and 32. Further, the user 2 may measure the ECG template 421 and store the ECG template 421 in the server 42 in advance. For the embodiment, the ECG template 151 is the same as the ECG template 421 for the same person, and both are corresponding to the two ECG signals 31 and 32.

The measuring device 1 further comprises a speaker unit 17 and a microphone 18 that are implemented in the casing 10 and are electrically connected with the microprocessor 13. For the embodiment, the measuring device 1 uses the circuit from the left hand to the left side of face of the user 2 to measure the first ECG signal 31, and then uses the circuit from the right hand to the right side of face of the user 2 to measure the second ECG signal 32. To inform the user 2 about the measurement being done and changing side of face to continuously measure, the microprocessor 13 controls the speaker unit 17 to make a reminding sound for reminding the user 2 to change a side for following processes.

For improving the security level of the embodiment, in addition to the first ECG signal 31 and the second ECG signal 32, the measuring device 1 can be further added the voice of the user 2 to be another parameter when engaging in the biometric authorization process. As shown in FIG. 5, the storing unit 15 stores voice data 152 pre-input by the user 2 when the user 2 enrolled in the system by the measuring device 1. Besides whether the input ECG and the ECG template 151 are matched or not, for higher level security, the input voice signal and the voice data 152 are compared with each other simultaneously. To implement, the storing unit 15 has saved a pre-measured voice signal via the microphone 18. Hence, based on the comparing result of the input ECG with the ECG template 151 and the comparing result of the input voice signal with the voice data 152, the user 2 can be determined as authorization or not.

Figure 6:
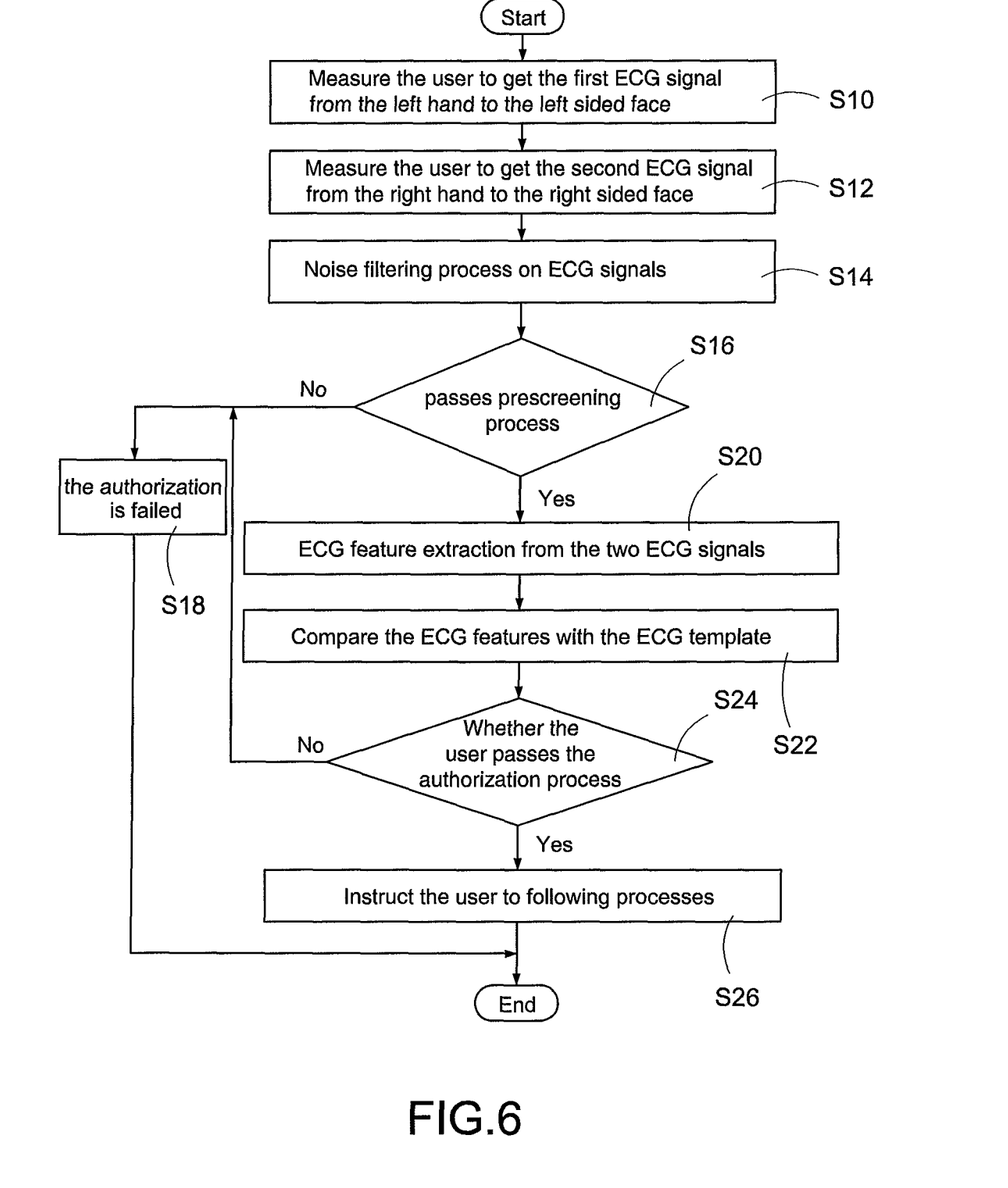
FIG. 6 illustrates a flow chart of an embodiment of the ECG measuring method of the present invention.

Please refer to FIG. 6, which illustrates a flow chart of an embodiment of the ECG measuring method of the present invention. The method comprises the steps that are listed below:

(S10) the measuring device 1 measures the user 2 to get the first ECG signal 31 from the left hand to the left side of face;

(S12) the measuring device 1 measures the user 2 to get the second ECG signal 32 from the right hand to the right side of face;

wherein, in step (S10), the user 2 applies the first electrode 11 to adhere to his left hand and the second electrode 12 to adhere to his left side of face by using the measuring device 1 to measure the first ECG signal 31; in step (S12), the user 2 uses the first electrode 11 to adhere to his right hand and the second electrode 12 to adhere to his right side of face by using the measuring device 1 to measure the second ECG signal 32; for the embodiment, the measuring device 1 is able to preset that the first ECG signal 31 must be measured first or the second ECG signal 32 must be measured first, but it is not limited thereto. For another embodiment, the measuring device 1 may be programmed by that the user 2 to define a sequence of measurement, or to use the detecting unit 19 to auto-determine if the present measurement is the first ECG signal 31 or the second ECG signal 32;

(S14) the measuring device 1 can alternatively apply noise filtering processes on the two ECG signals 31 and 32 for getting rid of unnecessary signal before the biometric authorization process, and the measuring device 1 can alternatively engage in signal amplifying, signal processing, analog/digital conversion, etc.;

(S16) the measuring device 1 can alternatively determine whether the first ECG signal 31 or the second ECG signal 32 passes prescreening processes. If either the first ECG signal 31 or the second ECG signal 32 cannot pass the prescreening process, the next step goes to step (S18);

(S18) when authorization is failed, a message is sent out or is shown on the display screen 14;

wherein the prescreening process is to compare the outlooks of the two ECG signals 31 and 32 with the outlooks of the ECG template 151. If there is a significant difference between the first ECG signal 31 or the second ECG signal 32 and the ECG template 151, the measuring device 1 may not further process for authorization. It has to be noted that the steps (S14) and (S16) are optional, and there is no any sequential relationship between the two steps;

(S20) the measuring device 1 extract the ECG features with a preset amount from the first ECG signal 31 and the second signal 32;

(S22) the measuring device 1 compares the ECG features with the ECG template 151;

the measuring device 1 extracts certain amount features by an algorithm such as the fracture point method. That is, an n ECG features are extracted from the first ECG signal 31, and another n ECG features are extracted from the second ECG signal 32. Then the 2n of ECG features are compared with the ECG template 151, and it will be described in detail later, wherein the proper amount of n is based on accuracy. Here n might be equal to 10 to 25, but it is not limited thereto;

(S24) according to the comparison result, the measuring device 1 determines whether the user 2 passes the authorization. If no, move to step (S18), that is, the authorization is failed and an error message is sent out; if yes, move to step (S26);

(S26) the measuring device 1 orders the user 2 to instruct the following processes;

wherein if the measuring device 1 is a portable phone, an authentication failed may cause screen-unlock calling and tel-bank forbidden, or lost connection to other devices, but it is not limited thereto.

Figure 7A:
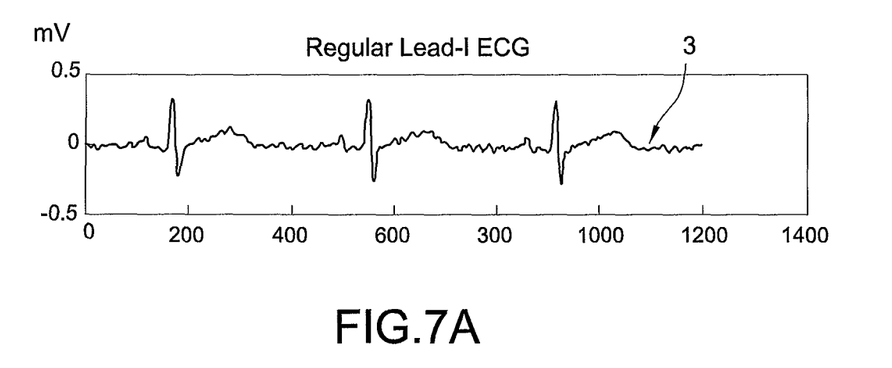
FIG. 7A illustrates a schematic complete Lead-I ECG of an embodiment of the ECG measuring device and the method thereof of the present invention.

Please refer to FIG. 7A to FIG. 7D, which illustrates a schematic complete Lead-I ECG of an embodiment of the ECG measuring device and the method thereof of the present invention, a schematic view of the first ECG signal of an embodiment of the ECG measuring device and the method thereof of the present invention, a schematic view of the second ECG signal of an embodiment of the ECG measuring device and the method thereof of the present invention, and ECG biometric feature of an embodiment of the ECG measuring device and the method thereof of the present invention. As shown in FIG. 7A, the complete clinical Lead-I ECG is plotted by measuring from the left hand to the right hand of a user. For the embodiment, it is a complete Lead-I ECG signal 3.

Figure 7B:
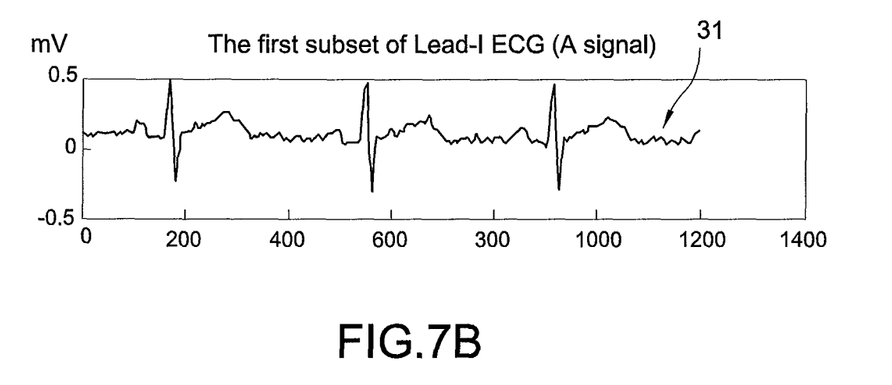
FIG. 7B illustrates a schematic view of the first ECG signal of an embodiment of the ECG measuring device and the method thereof of the present invention.
Figure 7C:
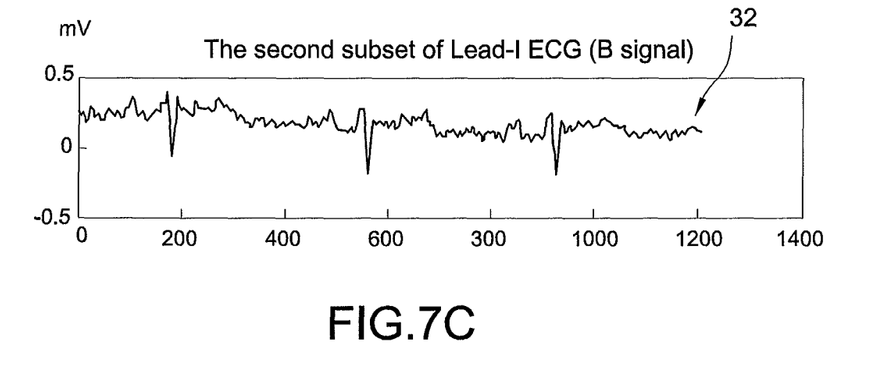
FIG. 7C illustrates a schematic view of the second ECG signal of an embodiment of the ECG measuring device and the method thereof of the present invention.

FIG. 7B is the first ECG signal 31, and FIG. 7C is the second signal 32. The present invention takes the head/face of a user located on a body center line, so the Lead-I circuit vector from the left hand to the right hand is divided into two parts, including from the left hand to the left side of face and from the right hand to the right side of face. As aforesaid, through the invented measuring method, the complete Lead-I ECG signal 3 is divided to the two ECG signals, including the first ECG signal 31 and the second ECG signal 32. However, the first ECG signal 31 plus the second ECG signal 32 is not equal to the complete Lead-I ECG signal 3 because of body natural characteristics. Since everybody has his unique characteristics, thus there is a remaining component other than signal 31 and 32 in aforesaid formula. The difference in the present invention is defined as a third ECG signal, which is a third ECG signal 33 in FIG. 14. The third ECG signal 33 can be another parameter for biometric authorization process, and it will be described later.

Figure 7D:
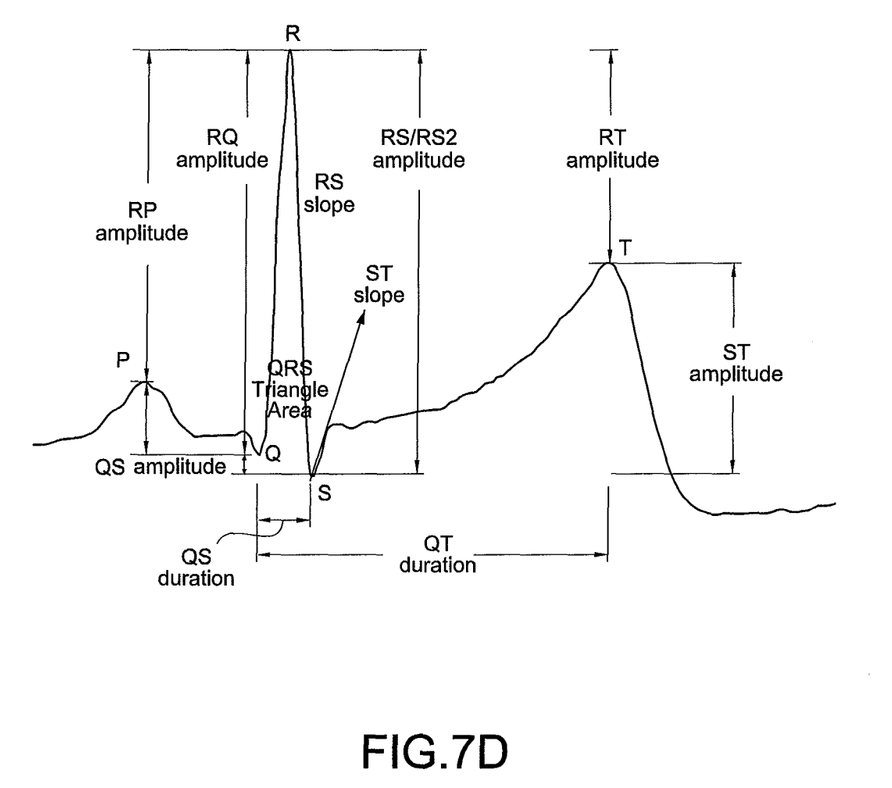
FIG. 7D illustrates ECG biometric feature of an embodiment of the ECG measuring device and the method thereof of the present invention.

FIG. 7D takes an ECG heartbeat of the complete Lead-I ECG signal 3 as an example in order to describe the ECG features. As shown in figure, each heartbeat has the fracture points P, Q, R, S, and T, and the relative positions among those points are various from person to person. This is a prior art and may not be described any further hereinafter. Depending on the fracture points and their relative positions, features are formed for the biometric authorization processes. Through aforesaid ECG feature extraction method, which is a prior art in the field and will not be described any further hereinafter. The ECG features extract from the ECG signals 3, 31, 32, and 33 are listed below:

| 1. | RQ amplitude |
| 2. | QS duration |
| 3. | RS amplitude |
| 4. | ST amplitude |
| 5. | QT duration |
| 6. | RS slope |

-continued

| | |
|---|---|
| 7. | QRS triangular area |
| 8. | RS amp./TS amp. |
| 9. | RS 2 amplitude |
| 10. | PQ amplitude |
| 11. | QS amplitude |
| 12. | RP amplitude |
| 13. | RT amplitude |
| 14. | ST slope |
| 15. | Angle Q |
| 16. | Angle R |
| 17. | Angle S |

Using the ECG feature extraction method, normally 17 ECG features can be obtained from the complete ECG signal 3, wherein "amplitude" is a height of amplitude between points, "duration" is a length of time between points, "slope" is a gradient, and "angle" is an angular magnitude. The amount of the ECG features may various based on different situations, so the number of features 17 is an example, but not limit to.

The present invention divides the complete Lead-I ECG signal 3 into the three components, including the first ECG signal 31, the second ECG signal 32, and the third ECG signal 33. By applying the ECG fracture point method, the measuring device 1 extracts at least 51 ECG features (17×3=51) from the three ECG signals 31, 32, 33, therefore the accuracy of identification is improved significantly. Moreover, other methods may only extract n ECG features from the complete Lead-I ECG signal, but the invented method is capable to extract at least 3n ECG features.

It has to be noted that interactive computing may also apply among the three ECG signals 31, 32 and 33. The methods may involve addition, subtraction and/or correlation coefficients between any two ECG signals from 31, 32, and 33. For example, an ECG signal can extract 17 ECG features. However, the three ECG signals 31, 32 and 33 may generate total of 54 ECG features (17×3+3=54). The extra three features come from addition, subtraction and correlation of signal 31 and 32. Aforesaid is only a preferred embodiment, but it is not limited thereto.

Additionally, the ECG signals 31, 32 and 33, from the user 2 can also be contains EMG (electromyography), EOG (electrooculogram), and an EEG (electroencephalogram) signals. If the measuring device 1 may apply signal separation methods to separate those signals. In addition, by experiment, the amplitude of the second ECG signal 32 contains clear respiratory patterns of the user 2 which can be further analyzed. By above signals, the emotion of the user 2 can be analysis on the measuring device 1 or the server 42. It may be provide an extra service or healthcare. It has to be noted that the second ECG signal 32 describes the right side of the user 2 body. Therefore, a medical staff may analyze specific diseases around the right side of the heart of the user 2.

Please refer to FIG. 8, which illustrates a schematic view of identification processes of an embodiment of the ECG measuring device and the method thereof of the present invention. The user 2 normally uses the measuring device 1 to make phone calls, and the measuring device 1 engages in measurement. When the measurement is done, the measuring device 1 directly engages in identification. If the identification is successful, the user 2 is capable to use the certain functions or to control a controlled device 41 connected with the measuring device 1. For the embodiment, the controlled device 41 can be a door lock or a car lock. It can be unlocked after the user 2 authorized, but it is not limited thereto.

The measuring device 1 is able to connect with a server 42 through Internet. The server 42 stores the ECG template 421 pre-measured by the user 2, and the measuring device 1 only measures the ECG signals 31, 32 and 33. The ECG can be transmitted to the server 42 which has capability to identify the user 2. The feature extraction from the ECG signals 31, 32 and 33 can be done by the server 42 as well, but it is not limited thereto. For the embodiment, the server 42 can be as a server of a shopping website or an Internet banking. When the identity authorization is done, the server accepts the access from the user 2, such as online shopping, online transfer, etc.

There is one thing to be noted. In addition to the light sensor or fingerprints, the detecting unit 19 can be a three-axial accelerator or a gyroscope. For example, the three-axial accelerator or the gyroscope has different read-out values when the two electrodes 11 and 12 are adhered to the left hand and the left side of face or the right hand and the right side of face respectively. In FIG. 3 or FIG. 4, the measuring device 1 can measure the angle via a gyroscope, the detecting unit 19. After calculation, the first ECG signal 31 or the second ECG signal 32 can be determined immediately.

For another embodiment, the measuring device 1 is able to determine the type of an ECG signals through an application program embedded therein. In practice, because most people have their hearts at the left side of the bodies, so the ECG amplitude of the first ECG signal 31 is larger than the wave amplitude of the second ECG signal 32 as shown in FIG. 7B and FIG. 7C. Hence, the measuring device 1 can analyze the amplitude of the ECG waveforms of the two ECG signals in order to distinguish which one is the first ECG signal 31 or the second ECG signal 32.

Figure 9:
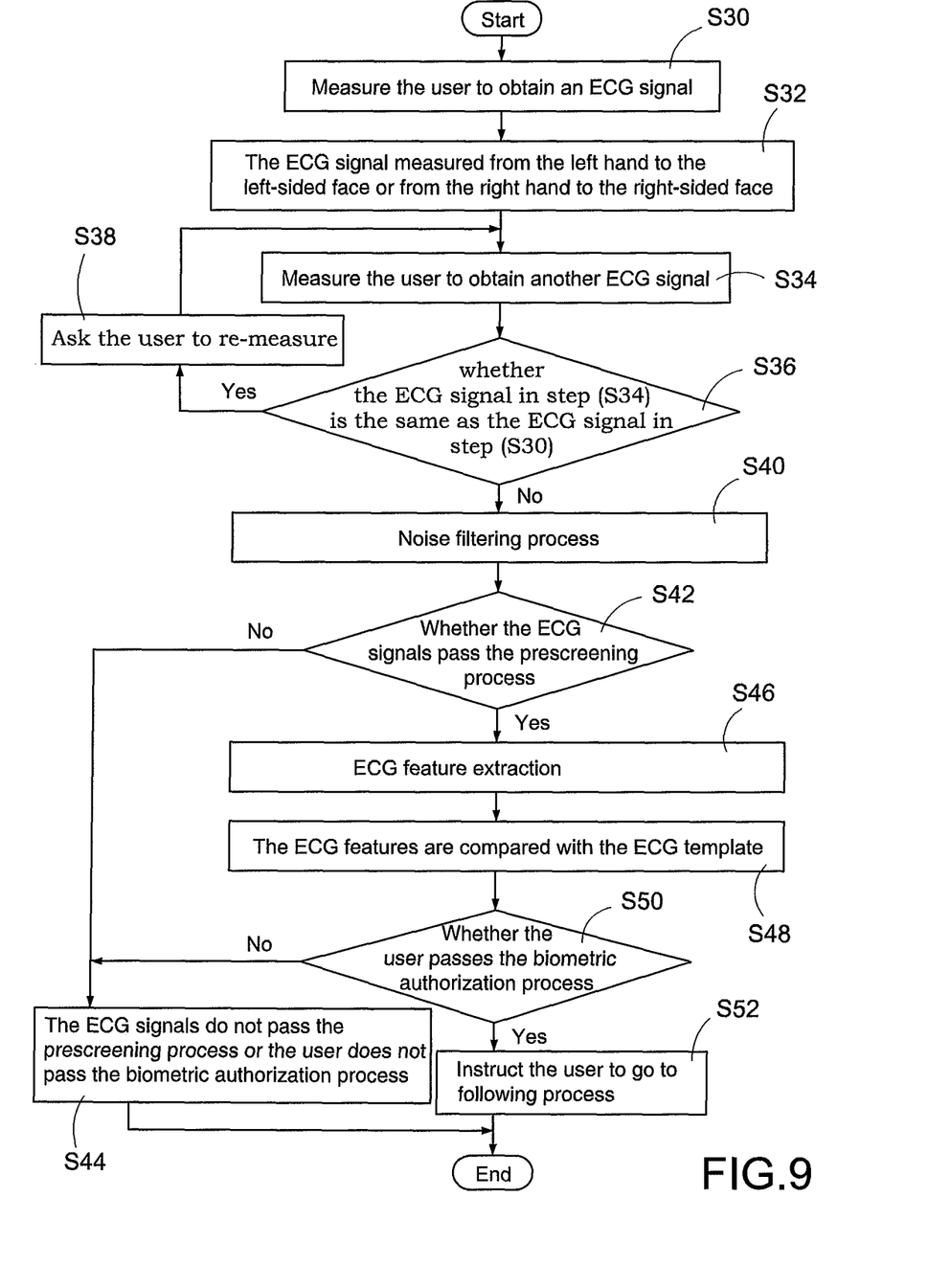
FIG. 9 illustrates a flow chart of authorization process with a plurality of ECG signals of an embodiment of the present invention.

Please refer to FIG. 9, which illustrates a flow chart of authorization process with a plurality of ECG signals of the present invention. The method comprises the steps listed below:

(S30) the measuring device 1 measures the user 2 in order to obtain an ECG signal;

(S32) via the detecting unit 19 or the application program, the ECG signal in step (S30) measured from the left hand to the left side of face or from the right hand to the right side of face is determined;

(S34) the measuring device 1 measures the user 2 in order to obtain another ECG signal;

(S36) via the detecting unit 19 or the application program, whether the ECG signal in step (S34) being not the same as the ECG signal in step (S30) is determined, if yes, the next step is moved to step (S38), if no, the next step is moved to step (S40);

wherein step (S36) is to determine whether the user changes a side to measure, that is, the condition of the measuring device 1 adhered to the left hand and the left side of face changes to the condition of the measuring device 1 adhered to the right hand and the right side of face, and vice versa, as a result, the measured two ECG signals being correct is assured, not that both are the first ECG signal 31 or the second ECG signal 32;

(S38) if the ECG signal measured in step (S34) is the same as the ECG signal measured in step (S30), the measuring device 1 outputs an instruction to ask the user 2 to re-measure;

when measuring the two ECG signals is done, the two ECG signals being the first ECG signal 31 and the second ECG signal 32 are assured, the following steps can be as the step (S14) to the step (S26) in FIG. 6 and are listed below:

(S40) the two ECG signals 31 and 32 are engaged in the noise filtering processes;

(S42) whether the two ECG signals 31 and 32 pass the prescreening process, if yes, the step is moved to step (S44), if no, the step is moved to step (S46);

(S46) a plurality of ECG features are extracted from the two ECG signals 31 and 32;

(S48) the input ECG are compared with the pre-stored ECG template 151;

(S50) according to the comparing result, whether the user 2 passes the biometric authorization process, if yes, the step is moved to step (S52), if no, the step is moved to step (S44);

(S44) if the two ECG signals 31 and 32 do not pass the prescreening process or the user 2 do not pass authorization; and (S52) the measuring device 1 orders the user 2 to go to following processes.

Figure 10:
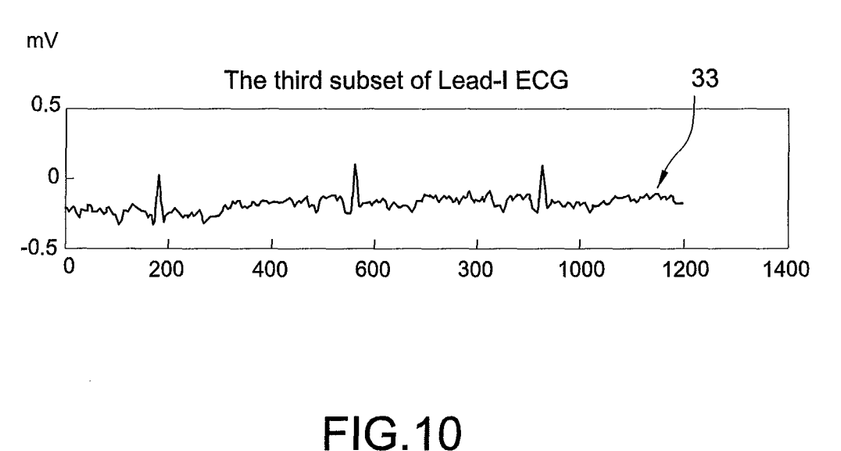
FIG. 10 illustrates a third ECG signal which is generated by substitution the first and second subset ECG signals from regular Lead-I ECG of an embodiment of the ECG measuring device and the method thereof of the present invention.

Please refer to FIG. 10, which illustrates a third ECG signal which is generated by substitution the first and second subset ECG signals from regular Lead-I ECG of an embodiment of the ECG measuring device and the method thereof of the present invention. The third ECG signal 33 can be another ECG biometrics. However, the third ECG signal 33 is not obtained from directly measuring the user, on the contrary, the third ECG signal 33 is obtained from calculating aforesaid formula.

Figure 11:
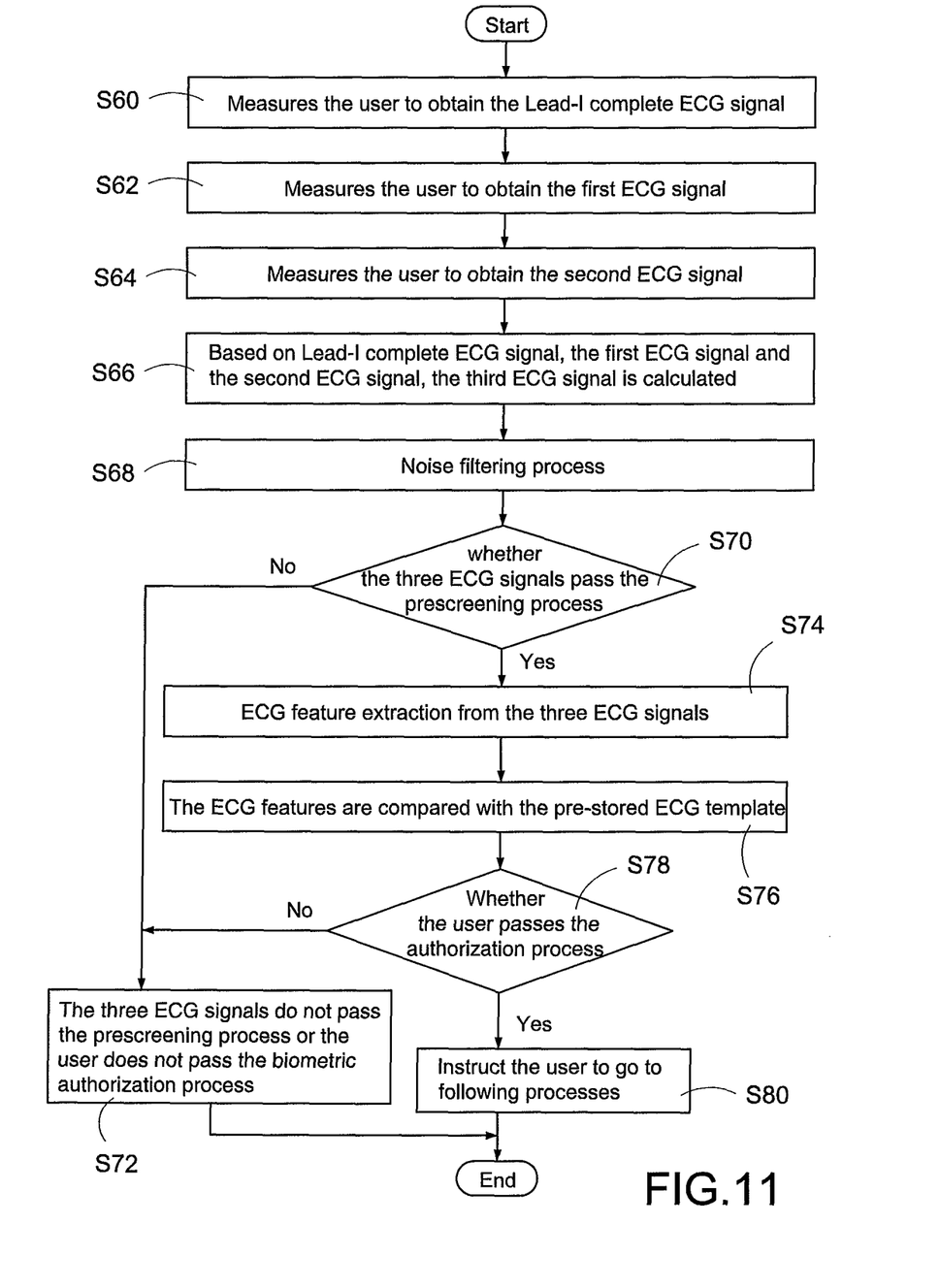
FIG. 11 illustrates a flow chart of a biometric process procedure of an embodiment of the ECG measuring method of the present invention.

Please refer to FIG. 11, which illustrates a flow chart of a biometric process procedure of an embodiment of the ECG measuring method of the present invention. If high security applications involve, the identify features should be applied as many as possible. The steps of the embodiment of the ECG measuring method of the present invention are listed below:

(S60) the measuring device 1 measures the user 2 to get the complete Lead-I ECG signal 3 from the left hand to the right hand of the user 2, or by other measuring devices, and the complete Lead-I ECG signal 3 is transmitted to the measuring device 1, but it is not limited thereto;

(S62) the measuring device 1 further measures the user 2 to get the first ECG signal 31;

(S64) the measuring device 1 further measures the user 2 to get the second ECG signal 32;

(S66) according to the complete Lead-I ECG signal 3, the first ECG signal 31 and the second ECG signal 32, the third ECG signal 33 is calculated by the measuring device 1, wherein the third ECG signal 33 is obtained from that the complete Lead-I ECG signal 3 which subtracts the sum of the first ECG signal 31 and the second ECG signal 32. For the embodiment, the first ECG signal 31, the second ECG signal 32 and the third ECG signal 33 will be engaged in the biometric authorization process, so the amount of the ECG template 151 or 421 stored in the measuring device 1 or the server 42 shall be at least three, and the three ECG templates are corresponding to the three ECG signals 31, 32 and 33, therefore the biometric authorization process can be engaged;

after step (S66), the following steps can be as the step (S14) to the step (S26) in FIG. 6 and are listed below:

(S68) the three ECG signals 31, 32 and 33 are engaged in the noise filtering processes;

(S70) whether the three ECG signals 31, 32 and 33 pass the prescreening process, if yes, the step is moved to step (S74), if no, the step is moved to step (S72);

(S74) a plurality of ECG features are extracted from the three ECG signals 31, 32 and 33;

(S76) the ECG features are compared with the pre-stored ECG template 151 or 421;

(S78) according to the comparing result, whether the user 2 passing the biometric authorization process is determined, if yes, the step is moved to step (S80), if no, the step is moved to step (S72);

(S72) if the three ECG signals 31, 32 and 33 do not pass the prescreening process or the user 2 do not pass authorization; and (S80) the measuring device 1 orders the user 2 to go to following processes.

There is one thing to be noted. For adding features for identification, the measuring device 1 can receive the input voice signal by the user 2 simultaneously, and when step (S76) is executed, the voice signal and the voice data 152 are compared to each other at the same time. As a result, the accuracy of identification is improved.

For the present invention, the measuring device 1 is used to measure the first ECG signal 31 and the second ECG signal 32; and the measuring device 1 or the server 42 engages in the biometric authorization processes and calculates the third ECG signal 33, but it is not limited thereto.

Although the invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. An electrocardiogram (ECG) measuring device, which measures subsets of Lead-I ECG vector, comprising:
    a first electrode, disposed at a lateral surface or a back surface of a body of the measuring device;
    a second electrode, disposed at a front surface of the body of the measuring device; and
    a microprocessor, electrically connected with the first electrode and the second electrode, the microprocessor capturing a first ECG signal when the first electrode and the second electrode touch the left hand and the left side of face of a user respectively, capturing a second ECG signal when the first electrode and the second electrode touch the right hand and the right side of face of the user respectively, and captures an entire ECG signal defined as a Lead-I ECG signal when the first electrode and the second electrode touch the left hand and right hand of the user respectively;
    wherein the microprocessor subtracts the first ECG signal and the second ECG signal from the entire ECG signal so as to obtain a third ECG signal, and engages the first ECG signal, the second ECG signal and the third ECG signal in a noise filtering process;
    wherein the microprocessor compares the first ECG signal, the second ECG signal and the third ECG signal with an ECG template, and determines whether the first ECG signal, the second ECG signal and the third ECG signal pass a prescreen process;
    wherein the microprocessor determines that the user does not pass a biometric authorization process if the first ECG signal, the second ECG signal and the third ECG signal do not pass the prescreen process, and the microprocessor extracts a first preset amount of ECG features from the first ECG signal, a second preset amount of ECG features from the second ECG signal, and a third preset amount of ECG features from the third ECG signal if the first ECG signal, the second ECG signal and the third ECG signal pass the prescreen process, and the user is engaged in the biometric authorization process according to the first preset amount, the second preset amount and the third preset amount of ECG features simultaneously.

2. The electrocardiogram (ECG) measuring device according to claim 1, wherein the first electrode and the second electrode are disposed at a casing or a display screen of the measuring device.

3. The electrocardiogram (ECG) measuring device according to claim 1 further comprising a storing unit, which is electrically connected with the microprocessor to store at least one ECG template premeasured by the user, the microprocessor comparing the ECG features with the ECG template for the user being engaged in the biometric authorization process.

4. The electrocardiogram (ECG) measuring device according to claim 3 further comprising:
- a speaker unit, electrically connected with the microprocessor, the microprocessor controlling the speaker unit to make a reminding sound when the first ECG signal and the second ECG signal are measured respectively;
- a microphone, electrically connected with the microprocessor, the measuring device receiving a voice signal input by the user through the microphone, the storing unit storing voice data pre-input by the user, the input voice signal and the existing voice data being compared with each other simultaneously when the user is engaged in the biometric authorization process by the microprocessor.

5. The electrocardiogram (ECG) measuring device according to claim 3 further comprising:
- at least one detecting unit, electrically connected with the microprocessor, the detecting unit determining that a present measurement is for the first ECG signal from the left hand to the left side of face of the user or the second ECG signal from the right hand to the right side of face of the user when measuring.

6. The electrocardiogram (ECG) measuring device according to claim 5, wherein the detecting unit is selected from the group consisted of: a three-axial accelerator, a gyroscope, fingerprints, and a light sensor.

7. The electrocardiogram (ECG) measuring device according to claim 1 further comprising:
- a transmitting unit, electrically connected with the microprocessor, the measuring device transmitting the ECG to an external serve via the transmitting unit, the server storing at least one ECG template pre-measured by the user and comparing the input ECG features with the ECG template for the user being engaged in the biometric authorization process.

8. An electrocardiogram (ECG) measuring method, which is applied to a measuring device, a body of the measuring device being disposed a first electrode and a second electrode, the first electrode touching the hands of a user, the second electrode touching the face of the user, the method comprising the steps of:
- (a01) measuring the user in order to capture an entire ECG signal, wherein the entire ECG signal is defined by measuring at Lead-I from the left hand to the right hand of the user;
- (a) measuring the use to capture a first ECG signal when the first electrode and the second electrode touch the left hand and the left side of face of the user respectively, and a second ECG signal when the first electrode and the second electrode touch the right hand and the right side of face of the user respectively, wherein the second ECG signal is different from the first ECG signal;
- (a11) after step (a), subtracting the first ECG signal and the second ECG signal from the entire ECG signal so as to obtain a third ECG signal;
- (a12) after step (a11), the first ECG signal, the second ECG signal and the third ECG signal being engaged in a noise filtering process;
- (a13) after step (a12), comparing the first ECG signal, the second ECG signal and the third ECG signal with an ECG template, and determining whether the first ECG signal, the second ECG signal and the third ECG signal pass a prescreen process;
- (a14) determining that the user does not pass a biometric authorization process if the first ECG signal, the second ECG signal and the third ECG signal do not pass the prescreen process;
- (b) extracting a first preset amount of ECG features from the first ECG signal, a second preset amount of ECG features from the second ECG signal and a third preset amount of ECG features from the third ECG signal respectively if the first ECG signal, the second ECG signal and the third EGG signal pass the prescreen process;
- (c) comparing the first preset amount, the second preset amount and the third preset amount of ECG features with the ECG template premeasured by the user simultaneously; and
- (d) determining whether the user passes the biometric authorization process according to the comparing result.

9. The electrocardiogram (ECG) measuring method according to claim 8, wherein step (a) comprises the steps of:
- (a21) capturing the first ECG signal;
- (a22) determining that the first ECG signal is captured by measuring from the left hand to the left side of face of the user or measuring from the right hand to the right side of face of the user;
- (a23) capturing the second ECG signal;
- (a24) determining whether the second ECG signal is different from the first ECG signal; and
- (a25) re-measuring the user if the second ECG signal is the same as the first ECG signal.

10. The electrocardiogram (ECG) measuring method according to claim 9, wherein the measuring device provides at least one detecting unit, in step (a22) and step (a24), via the detecting unit, the measuring device detecting that a measured ECG by the user is from the left hand to the left side of face or from the right hand to the right side of face.

11. The electrocardiogram (ECG) measuring method according to claim 9, wherein the measuring device provides an application program, in step (a22) and step (a24), via the application program, the measuring device analyzing the features of the waves of the first ECG signal and the second ECG signal, in order to determine that the first ECG signal and the second ECG signal are defined by measuring from the left hand to the left side of face of the user and measuring from the right hand to the right side of face of the user.

12. The electrocardiogram (ECG) measuring method according to claim 8 further comprising the steps of:
- (j) receiving a voice signal input by the user; and
- (k) comparing the voice signal with a voice data pre-input by the user;
- wherein the measuring device determines whether the user passes the biometric authorization process according to the comparing the input ECG features and the ECG template and the comparing the input voice signal and the pre-storing voice data.

* * * * *